United States Patent [19]

Walsh

[11] Patent Number: 4,561,430

[45] Date of Patent: Dec. 31, 1985

[54] LIGHT SOURCE FOR DIAGNOSTIC TEST

[76] Inventor: David J. Walsh, 2512 Mississauga Rd., Mississauga, Ontario, Canada, L5H 2L5

[21] Appl. No.: 637,632

[22] Filed: Aug. 3, 1984

[30] Foreign Application Priority Data

Jun. 11, 1984 [CA] Canada ................................. 456314

[51] Int. Cl.⁴ .............................................. A61B 1/06
[52] U.S. Cl. ..................................................... 128/6
[58] Field of Search .................... 128/4, 6, 8, 7, 9, 11, 128/13, 16, 18, 22; 362/109

[56] References Cited

U.S. PATENT DOCUMENTS

| | | | |
|---|---|---|---|
| 1,782,705 | 11/1930 | Armbruster | 128/11 X |
| 2,469,857 | 5/1949 | Allyn | 128/6 X |
| 3,281,637 | 10/1966 | Hultquist | 128/6 X |
| 3,349,764 | 10/1967 | Edinger et al. | 128/16 |
| 3,579,269 | 5/1971 | Ostensen | 128/6 X |
| 3,581,738 | 6/1971 | Moore | 128/6 |
| 3,592,199 | 7/1971 | Ostensen | 128/6 |
| 3,760,798 | 9/1973 | Edinger | 128/6 X |
| 4,406,280 | 9/1983 | Upsher | 128/11 |

OTHER PUBLICATIONS

*The Surgical Armamentarium*, A. V. Mueller, p. 207, © 1980.

Primary Examiner—William H. Grieb
Attorney, Agent, or Firm—Hirons, Rogers & Scott

[57] ABSTRACT

The invention provides a light source for use with diagnostic devices such as laparoscope having a male fitting to receive a light tube connection for transmitting light within the device to an end for viewing using an eyepiece on the device. The light source has an elongate casing and an electrical storage battery contained in the casing. The battery extends longitudinally and has first and second poles at opposite ends of the battery. A tubular insulating insert is positioned inside the casing at one of the ends of the casing and adjacent the first of the poles. A bulb is located in the insert and has the center terminal of the bulb in electrical connection with the first pole. First and second contacts are insulated from one another and located by the insert with the first contact coupled to the body of the bulb and the second contact coupled to the second pole. Both the contacts project slightly inwardly within the insert whereby when the light source is pushed over the male fitting, the light source is located on the diagnostic device and the male fitting completes the electrical circuit. The bulb is then powered so that light passes through the device to the end of the device.

7 Claims, 4 Drawing Figures

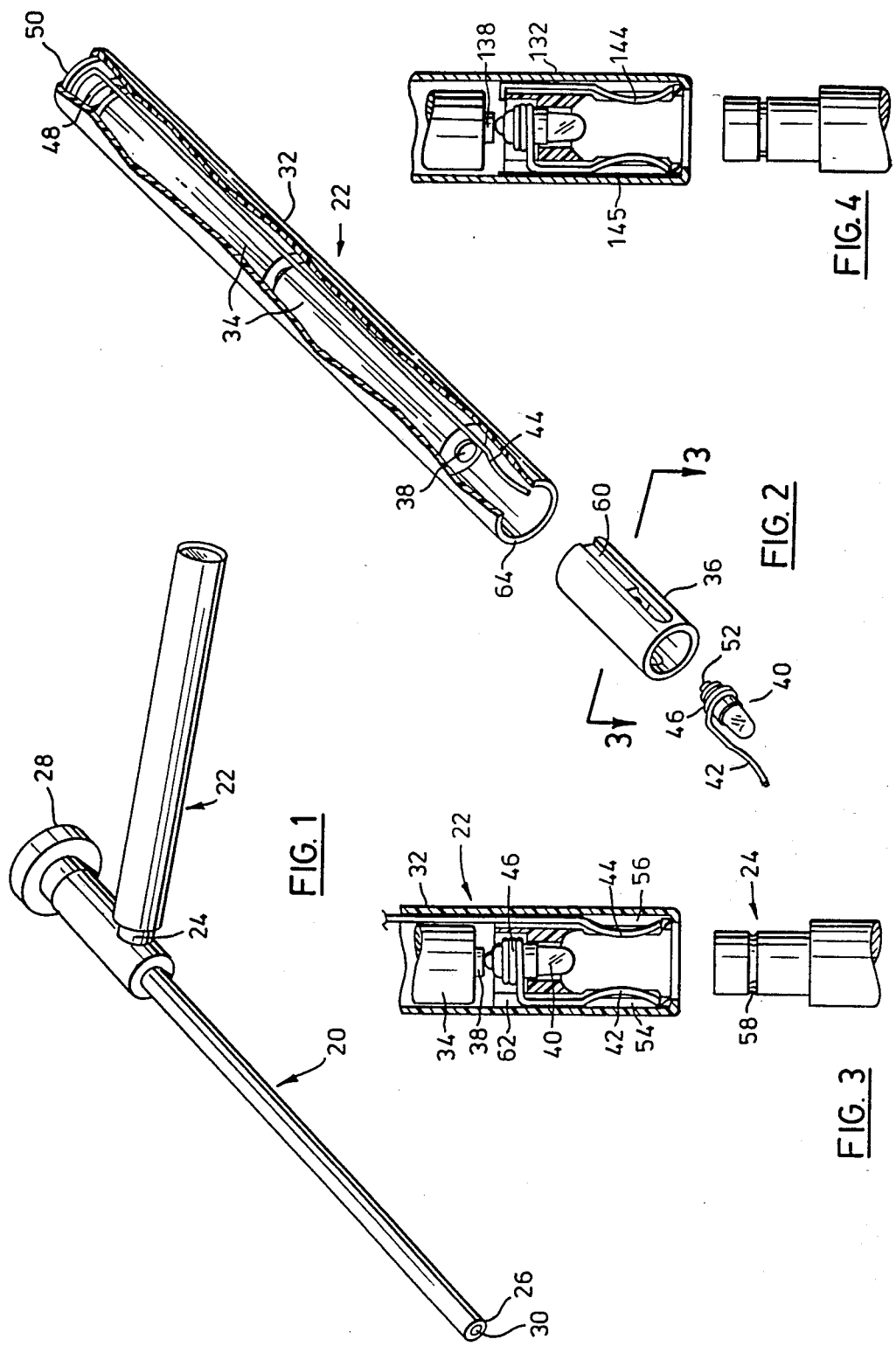

LIGHT SOURCE FOR DIAGNOSTIC TEST

This invention relates to diagnostic laparoscopes and similar devices used to inspect detail inside cavities, and more particularly to a light source for use with laparoscopes and such devices.

Although the invention will be described with reference to laparoscopes, it will be appreciated that the invention has uses with other devices requiring light sources for projecting light through light tubes contained in diagnostic devices generally.

Modern laparoscopes contain light tubes which lead from a fitting on the side of the laparoscope around the sight tube parts to project light from an annulus about an object lens at the end of the laparoscope.. The user can then look through the sight tube to inspect parts of the cavity illuminated by the light issuing from the annulus. Such conventional laparoscopes are used with a remote light source which is connected by a flexible light tube connector to the laparoscope. Such a combination of parts is entirely acceptable when the light source is located conveniently, but to have sufficient light sources to be available everywhere in a hospital would be prohibitively expensive. Consequently, the number of light sources in a hospital is limited. This inconvenience is highlighted by the fact that the laparoscope itself is quite portable and available readily for diagnostic purposes throughout the hospital.

Further, because of the mechanical connection between the light source and the laparoscope, there is a limit to its manoueverability.

It would be desirable to have a readily portable light source which can be used with a laparoscope for diagnostic purposes at least in a preliminary fashion so that should it be necessary for more detailed examination, the conventional high powered light source would be used. It is therefore a purpose of the present invention to provide a portable, pocket light source for use with a laparoscope and other similar devices, which is light, can be dedicated to use with a particular device such as a laparoscope, is inexpensive and disposable, and further is foolproof so that it is evident when it is "on" and "off".

Accordingly, the invention provides a light source for use with diagnostic devices such as laparoscopes having a male fitting to receive a light tube connection for transmitting light within the device to an end for viewing using an eyepiece on the device. The light source has an elongate casing and an electrical storage battery contained in the casing. The battery extends longitudinally and has first and second poles at opposite ends of the battery. A tubular insulating insert is positioned inside the casing at one of the ends of the casing and adjacent the first of the poles. A bulb is located in the insert and has the center terminal of the bulb in electrical connection with the first pole. First and second contacts are insulated from one another and located by the insert with the first contact coupled to the body of the bulb and the second contact coupled to the second pole. Both the contacts project slightly inwardly within the insert whereby when the light source is pushed over the male fitting, the light source is located on the diagnostic device and the male fitting completes the electrical circuit. The bulb is then powered so that light passes through the device to the end of the device.

The invention will be better understood with reference to the drawings in which:

FIG. 1 is a perspective view of an exemplary laparoscope with a preferred embodiment of a light source according to the invention coupled to the laparoscope;

FIG. 2 is a perspective view with parts broken away and exploded to illustrate details of the light source;

FIG. 3 is a sectional view on line 3—3 of FIG. 2 and drawn to a larger scale to show parts of the light source; and FIG. 4 is a view similar to FIG. 3 of an exemplary alternative embodiment of the light source.

Reference is made firstly to FIG. 1 which shows a conventional laparoscope 20 attached to a light source 22 according to a preferred embodiment of the invention. The light source is a snap fit over a male fitting 24 on the side of the laparoscope and this contains ends of light tubes which terminate at their opposite ends in an annular array 26 at the end of the laparoscope. The user looks through an eyepiece 28 which is associated with an optical system terminating at an object lens 30 within the annular array 26 so that light from the source 22 will illuminate detail to be examined at the end of the laparoscope.

Reference is next made to FIG. 2 to describe details of the light source 22. A casing 32 contains a battery made up of two cells 34 contained longitudinally in the casing in series with one another. An insulating insert 36 is tubular and fits snugly within an end of the casing adjacent a first pole 38 of the battery and is shaped to contain a bulb 40 and first and second contacts 42, 44 to permit completing the circuit when the source 22 is engaged on the male fitting 24 (FIG. 1) of the laparoscope.

The first contact 42 has a helical portion 46 for fitting firmly about the barrel of the bulb 40 and the second contact 44 extends past the battery inside the casing 32 terminating at an open-coiled portion 48. This portion engages with an end piece 50 contained in the casing to bias the cells 34 towards the bulb 40 for firm engagement between the first pole 38 and a centre contact 52 of the bulb, and also to make firm contact between the second pole (i.e. the end of the cell 34 adjacent the end piece 50) and the open-coiled portion 48.

The arrangement of the contacts 42, 44 and insert 36 will be better understood with reference to FIG. 3 which is drawn to a larger scale and shows the parts in an assembled condition with the male fitting 24 about to be engaged within the appropriate end of the light source 22. The contact 42 and contact 44 have inwardly curved end portions which project through respective supporting slots 54, 56 formed diametrically opposite one another adjacent an outer end of the insert 36. These portions of the inserts are then spaced from one another by a distance less than the diameter of the male fitting 24 so that when this is engaged the portions are deflected resiliently to locate mechanically in a groove 58 in the male fitting and to complete the circuit because the fitting is electrically conductive. On engaging the light source on the male fitting the light source is pushed until the leading end of the insert fits snugly on the base boss of the male fitting to give a positive mechanical location.

The insert 36 is grooved in alignment with the slots 54, 56 (as seen in FIG. 2 at 60). These grooves contain portions of the contacts and a further slot 62 is provided in alignment with slot 54 to give clearance for a radial portion of the contact 42 by which connection is made to the helical portion 46 where the contact engages the barrel or body of the bulb 40.

The contact 44 extends along the sides of the cells 34 so that these cells are slightly out of alignment with the bulb 40 which is centered with reference to the casing 32. However, this misalignment is minor and does not interfere with the connection between the first pole 38 of the battery and the bulb 40. The contact 44 continues along the sides of the cells as seen in FIG. 2 to terminate at the open-coiled portion 48 where contact is made with the second pole of the battery.

As shown in FIG. 2 the components are being assembled with an end 64 of the casing receiving the insert 36. Before engagement in the casing, the bulb 40 and contact 42 are assembled as shown in FIG. 2 and are then engaged in the insert 36 from the end nearer the casing 32. Once this sub-assembly has been completed, the contact 44 is also located in the insert before this contact and the cells are engaged completely in the housing. Once the insert 44 is in position, it is then used to push the cells 34 and contact 44 into the housing to take up the position shown in FIG. 3. Next, the outer end 64 of the light source is deformed into the position shown in FIG. 3 where it will be seen that it retains the insert to maintain the parts in their relative positions for use.

It will be evident that the casing 32 and insert should be of a material which is not electrically conductive so that these parts do not interfere with the electrical circuit which is completed by the insertion of the conductive male fitting 24.

It is also preferable to make the casing 32 and insert 36 from a transluscent thermosoftening synthetic plastic material so that when the circuit is completed, it is evident from the light source that the device is working. There is a slight glow seen through the casing and this acts as an indicator that the light is "on".

Other embodiments are contemplated by the invention. For instance that shown in FIG. 4 in which a casing 132 is made from a conductive material and an end piece (not shown but corresponding to end piece 50 of FIG. 2) is also conductive and makes contact with the second pole of the battery to the casing. A contact 144 extends only in the groove of the insert in contact with the casing and is therefore connected electrically to the second pole of the battery. The first pole 138 makes contact in the same way as shown in FIG. 3 but is insulated from the conductive casing 132 by a layer of insulating tape or the line 145 to avoid short circuiting the system. Variations of this kind are within the scope of the invention as described and claimed.

I claim:

1. A light source for use with diagnostic devices such as laparoscopes having a male fitting to receive a light tube connection for transmitting light within the device to an end for viewing using an eyepiece on the device, the light source comprising:
    an elongate casing;
    an electrical storage battery contained in the casing and extending longitudinally of the casing with first and second poles at opposite ends of the battery;
    a tubular insulating insert positioned inside the casing at one of the ends thereof and adjacent the first of the poles;
    a bulb located in the insert and having the centre terminal of the bulb in electrical connection with the first pole;
    first and second contacts insulated from one another and located by the insert, the first contact being coupled to the body of the bulb, and the second contact being coupled electrically to the second pole, both of the contacts projecting slightly within the insert whereby when the light source is pushed over the male fitting, the light source is located on the diagnostic device and the male fitting completes the circuit to power the bulb, so that light passes through the device to said end of the device.

2. A light source for releasable engagement on a male fitting of a laparoscope and the like to provide illumination at an end of the laparoscope, the light source comprising: a casing having a first end; battery means contained in the casing and having first and second poles; a bulb coupled to the casing and contained in the casing adjacent said first end; first and second contacts connected electrically to the bulb and to the battery means so that upon making connection with the male fitting of the laparoscope, the bulb lights; and means positioning the contacts separately inside the casing between the bulb and the first end of the casing for mechanical and electrical engagement with the male fitting of the laparoscope.

3. A light source as claimed in claim 1 in which the casing is of an insulating material and in which the second contact includes an open-coiled portion at the second pole to bias the battery into contact with the bulb.

4. A light source as claimed in claim 2 in which the casing is of an insulating material and in which the second contact includes an open-coiled portion at the second pole to bias the battery means into contact with the bulb.

5. A light source as claimed in claims 3 in which the casing is of a synthetic plastic material which is sufficiently transluscent to indicate to the user when the bulb is lit.

6. A combination of a laparoscope and a disposable light source, the laparoscope having a male fitting to provide illumination at an end of the laparoscope and the light source comprising: a casing having a first end engaged on the male fitting; battery means contained in the casing and having first and second poles; a bulb coupled to the casing between the male fitting and the battery means; first and second contacts connected electrically to the bulb, to the battery means, and to the male fitting of the laparoscope so that the bulb is lit; and means positioning the contacts separately inside the casing between the bulb and the first end of the casing where they are in mechanical and electrical engagement with the male fitting of the laparoscope.

7. The combination as claimed in claim 6 in which the casing is of an insulating material and in which the second contact includes an open-coiled portion at the second pole to bias the battery means into contact with the bulb.

* * * * *